United States Patent [19]

Nath

[11] Patent Number: 5,210,098
[45] Date of Patent: May 11, 1993

[54] USE OF PYRUVATE TO TREAT ACUTE RENAL FAILURE

[75] Inventor: Karl A. Nath, St. Louis Park, Minn.

[73] Assignee: Regents of the University of Minnesota, Minneapolis, Minn.

[21] Appl. No.: 841,879

[22] Filed: Feb. 26, 1992

Related U.S. Application Data

[63] Continuation of Ser. No. 585,984, Sep. 21, 1990, abandoned.

[51] Int. Cl.$^5$ .................. A61K 31/18; A61K 31/12
[52] U.S. Cl. .................................... 514/557; 514/675
[58] Field of Search ........................... 514/557, 675

[56] References Cited

U.S. PATENT DOCUMENTS

| | | | |
|---|---|---|---|
| 3,920,838 | 11/1975 | Flatt et al. ........................... | 514/400 |
| 4,100,161 | 7/1978 | Walser .................................. | 424/274 |
| 4,228,099 | 10/1980 | Walser ............................ | 206/501.11 |
| 4,415,556 | 11/1983 | Bretschneider ...................... | 424/153 |
| 4,663,166 | 5/1987 | Veech .................................. | 424/146 |
| 4,752,619 | 6/1988 | Walser et al. ........................ | 514/564 |

FOREIGN PATENT DOCUMENTS

| | | |
|---|---|---|
| 146474 | 6/1985 | European Pat. Off. . |
| 239357 | 9/1987 | European Pat. Off. . |

OTHER PUBLICATIONS

Remington's *Pharmaceutical Sciences*, A. Osol., ed., Mack Pub. Co. (16th ed. 1980) at pp. 1488-1493.
J. M. Weinberg et al., *FASEB J.*, 4, 3347 (1990).
Heyman et al., *JASN*, 2, 647 (1991).
R. C. Scaduto, Jr. et al., *Renal Physiol. Biochem.*, 14, 259 (1991).
R. A. Zager et al., *J. Lab. Clin. Med.*, 101, 130-140 (Jan., 1983).
A. D. Baines et al., *Am. J. Physiol.: Renal, Fluid and Electrolyte Physiol.*, 28, F80 (Jul. 1990).
P. Lamesch et al., *Transplant. Proc.*, 22, 518 (1990).
U. Leonhardt et al., *Transplant. Proc.*, 22, 720 (1990).
T. Yoshioka et al., *Kid. Int.*, 37, 497 (1990).
T. Yoshioka et al., *Kid. Int.*, 38, 282 (1990).
S. V. Shah, *Kid. Int.*, 35, 1093 (1989).
E. Melzer et al., *Biochem. J.*, 252, 913 (1988).
S. D. Varma et al., *Free Rad. Res. Comms.*, 4, 283 (1988).
M. Walser et al., *Kid. Int.*, 34, 859 (1988).
J. O'Donnell-Tormey et al., *J. Exp. Med.*, 165, 500 (1987).
L. Baud et al., *Am. J. Physiol.*, 251, F765 (1986).
U. Andrae et al., *Toxicol. Lett.*, 28, 93 (1985).
W. E. Mitch, *Ann. Rev. Med.*, 35, 249 (1984).
W. E. Mitch et al., *N. Engl. J. Med.*, 311, 623 (1984).
U. Dijkstra et al., *Neurology*, 34, 1493 (1984).
C. A. Bunton, *Nature*, 163 444 (1949).
M. J. Welsh et al., *J. Clin. Invest.*, 76, 1155 (1985).
M. S. Paller et al., *J. Clin. Invest.*, 74, 1156 (1984).
S. Bratell et al., *Acta Physiol. Scand.*, 134, 35 (1988).
H. Schneeberger et al., *Transplantation Proc.*, 21, 1245 (1989).
L. M. Gamelin et al., *Am. J. Physiol.*, 255, F450 (1988).
R. A. Zager et al., *Am. J. Physiol.*, 257, F953 (1989).
T. M. Hagen et al., *Kidney Int.*, 34, 74 (1988).
J. M. Messana, *Am. J. Physiol.*, 255, F874 (1988).
M. S. Paller et al., *Kidney Int.*, 33, 843 (1988).
R. S. Scaduto et al., *Am. J. Physiol.*, 255, F911 (1988).
S. Parthasarathy et al., *J. Clin. Invest.*, 77, 641 (1986).
J. E. Bird et al., *J. Clin. Invest.*, 81, 1630 (1988).

*Primary Examiner*—Frederick E. Waddell
*Assistant Examiner*—T. J. Criares
*Attorney, Agent, or Firm*—Merchant, Gould, Smith, Edell, Weller & Schmidt

[57] ABSTRACT

A therapeutic method is provided to arrest or prevent acute kidney failure by administration of a non-toxic pyruvate salt to a patient in need of such treatment.

11 Claims, No Drawings

USE OF PYRUVATE TO TREAT ACUTE RENAL FAILURE

This invention was made with Government support under NIH Grant R29-DK38767. The Government has certain rights in this invention.

This is a continuation of application Ser. No. 07/585,984, filed Sep. 21, 1990, which was abandoned upon the filing hereof.

BACKGROUND OF THE INVENTION

The classification of cessation of renal function into acute and chronic renal failure demarcates disease states that are distinct in etiology, pathogenesis, rate of loss of renal function, potential for recovery of renal function and therapeutic strategies applied in their management. Chronic renal failure is characterized by an inexorable loss of renal function, which can last for several years after the initial presentation of renal insufficiency, culminating in end-stage disease. The arrival of end-stage disease signifies irretrievable loss of renal function and necessitates replacement of renal function by dialysis or transplantation. The leading causes of chronic renal failure are assorted glomerulonephritides, diabetic nephropathy, chronic tubulointerstitial diseases and polycystic kidney diseases. See F. N. Ziyadeh, *Textbook of Internal Medicine*, Vol. 1, W. E. Kelley, ed., J. B. Lippincott Co., Philadelphia (1989) at pages 883–889; M. Walser, *Kid. Int.*, 37, 1195 (1990).

Management of patients with chronic renal failure utilizes strategies that retard the rate of loss of renal function, thereby delaying the onset of end-stage disease. Such therapeutic strategies include treatment of systemic hypertension, correction of perturbed calcium/phosphate homeostasis and restriction in dietary protein intake (W. E. Mitch, *Ann. Rev. Med.*, 35, 249 (1984)). Some studies have indicated that dietary supplementation with alpha-keto acids in conjunction with restricted protein and phosphate intake may be efficacious in retarding the progression of established renal disease (W. E. Mitch et al., *N. Engl. J. Med.*, 311, 623 (1984)). The mechanism by which dietary supplementation with alpha-keto acids may act to alleviate progressive renal injury is unknown.

Acute renal failure is characterized by a relatively abrupt decline in renal function. Temporary replacement of renal function by dialysis may be indicated within days of the instigating insult and may be necessary for several weeks during the maintenance phase of acute renal failure. While recovery of renal function usually occurs, there is substantial morbidity and mortality during the initiation, maintenance and recovery phases of acute renal failure. The recovery phase of acute renal failure, once complete, usually allows the resumption of normal renal function. Conditions that predispose to acute renal failure include ineffective renal perfusion, systemic hypotension of any cause, sepsis, major trauma, nephrotoxic insults such as aminoglycoside antibiotics and radiographic contrast agents, and obstruction to the urinary tract (M. Brezis et al., *The Kidney*, B. M. Brenner et al., eds., W. B. Saunders (3rd ed. 1986) at pages 735–799). Less commonly, acute renal failure may arise from certain types of glomerulonephritis and vasculitis.

Since there are no specific therapeutic maneuvers that consistently and effectively hasten the recovery of renal function, once acute renal failure has already occurred, the management of patients with acute renal failure emphasizes the avoidance and/or correction of conditions such as hypoperfusion, hypotension, sepsis and nephrotoxic agents that predispose to acute renal failure (C. M. Kjellstrand et al., *Diseases of the Kidney*, R. W. Schrier et al., eds., Little Brown Co., Boston (4th ed. 1988) at pages 1501–1542).

Therefore, there is a continuing need for effective therapies to arrest or prevent acute renal failure in susceptible patients.

SUMMARY OF THE INVENTION

The present invention provides a therapeutic method comprising administration of an amount of a pyruvate salt to a patient experiencing, or in danger of, acute renal failure. The pyruvate salt, preferably sodium pyruvate, is preferably dispersed or dissolved in a pharmaceutically acceptable liquid carrier and administered parenterally in an amount effective to arrest or prevent said acute renal failure, thus permitting restoration of normal kidney function. In some cases, the pyruvate may be infused directed into the kidney or into the proximal renal arterial circulation. The present method is effective to prevent or counteract acute kidney failure due to a wide variety of causes, including, but not limited to, traumatic injury, including burn injury and obstruction; reperfusion following ischemia, inflammatory glomerulonephritis, and sepsis, e.g., due to gram negative bacterial infection.

The present invention also provides a blood-free protective aqueous solution comprising an amount of a pyruvate salt effective to perfuse and protect an isolated ("ex vivo") ischemic, "donor" kidney from injury which may occur upon reperfusion of blood following reimplantation into a human recipient. These protective solutions also can comprise sugars, nucleosides or nucleoside bases, electrolytes and other protective agents known to the art. A further aspect of the invention is a method to protect an ex vivo, ischemic kidney from reperfusion injury following reimplantation in a human donor comprising perfusing or otherwise contacting said kidney with the above-described protective solution.

DETAILED DESCRIPTION OF THE INVENTION

There is mounting evidence that increased renal generation of reactive oxygen species provides a common pathogenic pathway by which acute renal damage may arise in diverse clinical circumstances (L. Baud et al, *Am. J. Physiol*, 251, F765–766 (1986); S. V. Shah *Kid. Int.*, 35, 1093 (1989)). These partially reduced forms of oxygen such as superoxide anion, hydrogen peroxide ($H_2O_2$) and the hydroxyl anion are toxic to renal tissue. Hydrogen peroxide possesses certain characteristics that render increased generation of this species particularly damaging to the kidney. Firstly, hydrogen peroxide is a precursor to other reactive oxygen metabolites including hydroxyl ion, one of the most reactive and injurious chemical species known. Secondly, hydrogen peroxide is readily diffusible throughout intracellular and extracellular compartments and thus may inflict injury to cellular domains distant from the site of generation of hydrogen peroxide. A number of studies have confirmed the capacity of pyruvate and other alpha-keto acids to degrade hydrogen peroxide while these acids concomitantly undergo non-enzymatic decarboxylation. For example, see C. A. Burton, *Nature*, 163, 444

(1949) and E. Melzer et al., *Biochem. J.*, 252, 913 (1988). Yet no more than a handful of studies, all conducted in vitro, have examined whether such scavenging effects of pyruvate and alpha-keto acids exerts cytoprotection against peroxide-induced oxidant stress. Equimolar amounts of alpha-ketoglutarate diminish the toxicity exerted by $H_2O_2$ on V79 Chinese hamster cells, while equimolar quantities of pyruvate completely prevented such toxicity (U. Andrae et al., *Toxicol. Lett.*, 28, 93 (1985). The cytoprotective properties of pyruvate against peroxideinduced injury is also exhibited in malignant murine cell lines. (J O'Donnell-Tormey et al., *J. Exp. Med.*, 165, 500 (1987). Hydrogen peroxide and other oxidants impair solute transport in the lens and such pathologic effects have been implicated in the pathogenesis of lenticular cataracts. The presence of pyruvate in the culture medium bathing the lens attenuates the decline in lenticular epithelial transport induced by $H_2O_2$. S. D. Varma et al., *Free Rad. Res. Comm.*, 4, 283 (1988). However, there have been no reports of the ability of pyruvate to scavenge peroxide in vivo to any extent. Therefore, my discovery that administration of a pyruvate salt provides an effective therapeutic approach to the treatment of acute renal failure could not have been predicted from these literature reports. For example, administration of sodium pyruvate was demonstrated to be protective using multiple in vivo models of renal injury including 1) hydrogen peroxide-induced proteinuria, a model for inflammatory glomerulonephritis, 2) ischemia-reperfusion injury, and 3) glycerol-induced acute renal failure.

Hydrogen peroxide-induced proteinuria.

Inflammatory glomerulonephritides are characterized by increased leakage of protein across the glomerular filtration barrier. S. V. Shah, *Kid. Int.*, 35, 1093 (1989). The appearance of relatively large amounts of protein in the urine is the hallmark of glomerular injury. In such conditions, the glomerulus displays proliferation of intrinsic glomerular cells and is invaded by inflammatory cells. Such cellular activity can generate increased amounts of reactive species including hydrogen peroxide.

Systemic infusion of pyruvate prior to and during the intrarenal infusion of hydrogen peroxide was found to prevent injury to the glomerular filtration barrier that leads to the leakage of protein into the urinary space. This result directly demonstrates that pyruvate protects against peroxide-induced proteinuria, as more fully set forth in the following example.

EXAMPLE I.

Effect of Pyruvate on Hydrogen Peroxide-Induced Proteinuria In Vivo

Renal clearance studies of the left kidney were performed under euvolemic conditions as previously described. K. A. Nath et al., *J. Clin. Invest.*, 76, 667 (1985). A 34 gauge stainless steel Hamilton needle was inserted into the orifice of the left renal artery. The position of the tip of the needle was verified by an injection of lissamine green. Glomerular filtration rate (GFR), renal plasma flow rates, mean arterial pressure and urinary protein excretory rates were first determined in the basal state for two consecutive thirty-minute periods following an intra-renal infusion of $H_2O_2$ in the left renal artery. Thirty micromoles of $H_2O_2$ was infused over one-half hour. Such infusions of $H_2O_2$ have been shown to induce markedly increased rates of urinary protein excretion. T. Yoshioka et al., *Kid. Int.*, 37, 497 (1990); 38, 282 (1990).

Prior to infusing $H_2O_2$, rats received a bolus of sodium pyruvate (Sigma Chemical Co., St. Louis, Mo.) (1 ml/Kg body weight of a 4% solution of sodium pyruvate in distilled water) given over 5 minutes followed by a maintenance infusion of 0.5 ml/hr. This dose was calculated to achieve a plasma level of 500 $\mu$M assuming a volume of distribution of 60% body weight. Control rats received normal saline in identical volumes.

In control rats, $H_2O_2$ induced markedly increased urinary protein excretory rates as compared to such excretory rates in the basal period, $139.6\pm23.7$ vs. $8.2\pm2.3$ $\mu$g/min, p<0.01. This striking increment in protein excretion occurred in the absence of significant changes in mean arterial pressure ($126\pm4$ vs. $127\pm4$ mmHg), in glomerular filtration rate (GFR) ($1.43\pm0.05$ vs. $1.31\pm0.07$ ml/min), or renal plasma flow rates ($5.56\pm0.39$ vs. $6.39\pm0.31$ ml/min). Pretreatment with sodium pyruvate prevented the rise in urinary protein excretory rates induced by hydrogen peroxide, $12.3\pm1.8$ vs. $39.6\pm16.2$ $\mu$g/min, p=ns, without any significant alteration in mean arterial pressure ($125\pm8$ vs. $124\pm8$ mmHg), GFR ($1.50\pm0.05$ vs. $1.33\pm0.07$ ml/min), or renal plasma flow rates ($5.88\pm0.33$ vs. $5.82\pm0.47$ ml/min). Basal renal hemodynamics and mean arterial pressures in rats pretreated with pyruvate were not significantly different from the control rats.

Ischemia-Reperfusion Injury

This model is the experimental analog of acute renal failure, such as occurs when the kidney is rendered ischemic by blood loss, circulatory collapse of any cause, cross-clamping of the aorta and acute tubular necrosis of the transplanted kidney following cadaveric renal transplant. M. S. Paller et al., *J. Clin. Invest.*, 74, 1156 (1984). In this model, ischemia is induced by removal of the right kidney and ischemic clamping of the left kidney for 45 minutes. Systemic administration of pyruvate prior to and during the induction of ischemia-reperfusion injury of the kidney leads to improvement of renal function as measured by glomerular filtration rate and renal blood flow.

In another model of ischemia-reperfusion injury induced by cross clamping of the aorta, the administration of pyruvate was associated with diminished mortality and improved renal function upon reperfusion. Extrapolating from these studies, it is expected that such administration of pyruvate would similarly protect against acute renal failure in the above-listed clinical circumstances as well as acute renal failure following cadaveric renal transplantation. In the latter situation, the cadaveric donor kidney is maintained ex vivo by preservation solutions. Acute renal failure in transplanted cadaveric kidneys is commonly encountered and contributes to morbidity in the post-transplant setting. L. H. Toledo-Pereyra, *Contr. Nephrol.*, 71, 129 (1989). The inclusion of pyruvate in such preservative solutions would provide an efficient scavenger for harmful reactive species that may be generated following reimplantation and thereby minimize the risk for acute renal failure in this setting.

EXAMPLE II

Effect of Pyruvate on Renal Function Using In Vivo Ischemia—Reperfusion Injury Model The protective role of sodium pyruvate was assessed in two in vivo models. In the first, rats underwent ligation of the right renal artery and 45 minutes left renal artery occlusion (RAO study). In the second study, the abdominal aorta above the celiac axis was occluded for 15 minutes (AO study). Prior to occlusion, 12% aqueous sodium pyruvate (Pyr) (1 ml/kg followed by 0.5 ml/h) or equimolar glucose (Glu) was infused. The basal glomerular filtration rate (GFR) in Pyr and Glu rats was similar in the two models. GFR (left kidney) in the RAO study was improved in Pyr rats, as shown in Table I, below.

TABLE I

| | RAO Study GFR (minutes after reflow) | | | |
|---|---|---|---|---|
| | (0–30 min) | (30–50 min) | (50–70 min) | (70–90 min) |
| Glu (n = 6) | 0.07 ± 0.03 | 0.14 ± 0.05 | 0.15 ± 0.05 | 0.11 ± 0.04 |
| Pyr (n = 6) | 0.15 ± 0.03 | 0.36 ± 0.05* | 0.40 ± 0.05* | 0.39 ± 0.04* |

*Results: Means ± SE, ml/min, $p < 0.05$, Pyr vs. Glu.

Pyr-treated rats also demonstrated increased renal blood flow (RBF) (2.51±0.67 vs. 5.60±0.79 ml/min) and lesser reduction in transport maximum for para-aminohippurate from basal values (0.45±0.03 vs. 0.36±0.02 mg/min) without differences in arterial pressure, hematocrit or plasma osmolality. Blood (Pyr) was increased in Pyr rats (141±10 vs. 416±21 μM).

Improved GFR was also noted upon reflow in the AO study, as shown by the data in Table II, below.

TABLE II

| | AO Study GFR (minutes after reflow) | | | |
|---|---|---|---|---|
| | (0–30 min) | (30–60 min) | (60–90 min) | (90–120 min) |
| Glu (n = 5) | 0.51 ± 0.09 | 0.400 ± 0.10 | 0.19 ± 0.11 | 0.07 ± 0.06 |
| Pyr (n = 5) | 0.99 ± 0.11* | 1.22 ± 0.16* | 0.91 ± 0.17* | 0.66 ± 0.21* |

*Results: Means ± SE, ml/min, $p < 0.05$, Pyr vs. Glu

By 150 minutes of reflow, four deaths occurred in Glu rats with only one death in Pyr rats (mean GFR in Pyr rats, 0.46±0.16 ml/min). Thus, Pyr markedly improves renal function in two in vivo models of ischemia-reperfusion injury.

EXAMPLE III

Glycerol-induced acute renal failure

This model, induced by the intramuscular injection of hypertonic glycerol into dehydrated rats leads to acute renal failure accompanied by myoglobinemia and myoglobinuria. The injured kidney displays acute tubular necrosis and prominent cast formation. This model represents acute renal failure as occurring after muscle injury (the syndrome described as rhabdomyolysis), after extensive major trauma and following major burns. A. Dubrow et al., *Acute Renal Failure*, B. M. Brenner et al., eds., Churchill Livingston (2d ed. 1988) at pages 279–294. Using this model, we have demonstrated that treatment with sodium pyruvate, but not with equimolar amounts of glucose or sodium chloride, led to improved renal function as measured by glomerular filtration rate. Interestingly, the protective effects of pyruvate were derived, at least in part, from the attenuation of muscle necrosis, itself a free radical dependent mechanism, since creatine phosphokinase activity was reduced in the rats treated with pyruvate.

Such functional improvement was observed acutely, for 3 hrs, after administration of intramuscular glycerol, and also at a later time point, that is, 24 hrs after glycerol. Morphometric studies of kidney structure 24 hrs after glycerol administration displayed marked attenuation in renal damage in rats treated with pyruvate, but not in rats treated with saline. Thus, pyruvate protects against both functional and structural damage in this model. These findings lead to the suggestion that the administration of pyruvate would protect against acute renal failure in clinical settings attended by muscle necrosis, other forms of tissue injury, trauma and burns.

Dosage Forms

In in vivo studies, dosages of sodium pyruvate that have proved effective in protecting against acute renal injury have included a loading dose of a 4, 8 or 12% solution of sodium pyruvate solution first given at a dose of 1 ml/Kg body weight followed by 0.5 ml per hour as an infusion. Using a 12% solution (approximately 1 molar), a three-fold elevation in circulating blood pyruvate levels was observed, without significant changes in serum osmolality, mean arterial pressure or renal function of the intact, non-injured kidney. Available in the literature is one study in humans reported by V. Dijkstra et al., *Neurology*, 34, 1493 (1984), that employed an infusion of sodium pyruvate (500 mg/kg body weight given as a 1 Molar solution over 10 minutes). This infusion was employed to test the hypothesis that patients with Friedreich's ataxia exhibit a defect in pyruvate metabolism. In this study, such administration of sodium pyruvate was associated with a peak level of approximately 2 millimolar in control subjects and 4.7 millimolar in patients with Friedreich's ataxia. It should be emphasized that in neither group were there any adverse effects.

Based on Examples I–III above, as well as the established non-toxic effect of the administration of pyruvate in humans by Dijkstra et al., in the acute clinical circumstances outlined above, a bolus dose of about 0.5–1.5 ml/kg body weight of a 10–15% aqueous sodium pyruvate solution followed by a maintenance infusion of 50–150 ml/hr of a 250–300 millimolar sodium pyruvate solution (that is, a solution approximately isotonic with plasma) can be employed. The exact rate of infusion will be dictated by the volume status of the patient. Pyruvate is also an effective protectant when added to solutions employed to preserve cadaveric kidneys, or kidneys removed from living donors and intended for transplantation, using concentrations in the 1–5 millimolar range.

Although the invention has been exemplified by reference to sodium pyruvate, other nontoxic alkali metal, alkaline earth metal, ammonium and substituted amine salts of pyruvic acid can also be employed.

All of the documents cited hereinabove are incorporated by reference herein.

The invention has been described with reference to various specific and preferred embodiments and techniques. However, it should be understood that many variations and modifications may be made while remaining within the spirit and scope of the invention.

What is claimed is:

1. A therapeutic method comprising parenterally administering an amount of a pyruvate salt to a patient experiencing the abrupt decline in renal function associated with acute renal failure, which amount is effective to treat said renal failure.

2. The method of claim 1 wherein said pyruvate salt is sodium pyruvate.

3. The method of claim 1 wherein said acute renal failure is due to traumatic injury.

4. The method of claim 1 wherein said acute renal failure is due to reperfusion of the kidney with blood following ischemia.

5. The method of claim 1 wherein said acute renal failure is due to inflammatory glomerulonephritis.

6. The method of claim 1 wherein said acute renal failure is due to sepsis.

7. The method of claim 1 wherein a solution of said pyruvate is infused directly into the kidney.

8. The method of claim 2 wherein said solution comprises about 1-5 millimolar sodium pyruvate.

9. A method comprising treating repersion injury to an isolated, ischemic human kidney following reimplantation into a human recipient by perfusing said kidney with with an aqueous solution comprising an effective protectant amount of a pyruvate salt.

10. The method of claim 9 wherein the aqueous solution comprises about 1-5 millimolar sodium pyruvate.

11. The method of claims 1, 2 or 7 wherein said amount comprises a bolus dose of about 0.5-1.5 ml/kg body weight of said patent of an about 10-15% aqueous pyruvate solution, followed by infusion of 50-150 ml/hr of an about 250-300 millimolar pyruvate solution.

* * * * *